United States Patent
Schroff et al.

(10) Patent No.: US 10,487,333 B2
(45) Date of Patent: Nov. 26, 2019

(54) COMBINATION COMPRISING IMMUNOSTIMULATORY OLIGONUCLEOTIDES

(71) Applicant: MOLOGEN AG, Berlin (DE)

(72) Inventors: Matthias Schroff, Berlin (DE); Manuel Schmidt, Berlin (DE); Kerstin Kapp, Berlin (DE); Alfredo Zurlo, Berlin (DE)

(73) Assignee: Mologen AG, Berlin (DE)

( * ) Notice: Subject to any disclaimer, the term of this patent is extended or adjusted under 35 U.S.C. 154(b) by 0 days.

(21) Appl. No.: 15/756,798

(22) PCT Filed: Sep. 9, 2016

(86) PCT No.: PCT/EP2016/071314
§ 371 (c)(1),
(2) Date: Mar. 1, 2018

(87) PCT Pub. No.: WO2017/042336
PCT Pub. Date: Mar. 16, 2017

(65) Prior Publication Data
US 2018/0251767 A1 Sep. 6, 2018

(30) Foreign Application Priority Data
Sep. 9, 2015 (LU) .......................................... 92821

(51) Int. Cl.
| | | |
|---|---|---|
| *C12N 15/117* | (2010.01) | |
| *C12N 15/11* | (2006.01) | |
| *A61K 39/395* | (2006.01) | |
| *C07K 16/28* | (2006.01) | |
| *C07K 16/30* | (2006.01) | |
| *A61P 35/00* | (2006.01) | |
| *A61K 31/7088* | (2006.01) | |
| *A61K 39/00* | (2006.01) | |

(52) U.S. Cl.
CPC ........ *C12N 15/117* (2013.01); *A61K 31/7088* (2013.01); *A61K 39/3955* (2013.01); *A61K 39/39541* (2013.01); *A61P 35/00* (2018.01); *C07K 16/2818* (2013.01); *C07K 16/2827* (2013.01); *C07K 16/30* (2013.01); *C12N 15/111* (2013.01); *A61K 2039/505* (2013.01); *C12N 2310/17* (2013.01); *C12N 2310/32* (2013.01); *C12N 2310/344* (2013.01); *C12N 2310/531* (2013.01); *C12N 2310/532* (2013.01); *C12N 2320/31* (2013.01)

(58) Field of Classification Search
CPC ............ A61K 39/3955; A61K 2300/00; A61K 2039/505; A61P 35/00; C12N 15/111; C12N 15/117

USPC ..... 435/6.1, 91.1, 91.31, 455, 458; 514/1, 2, 514/44; 530/300, 350, 387.1; 536/23.1
See application file for complete search history.

(56) References Cited

U.S. PATENT DOCUMENTS

| | | | |
|---|---|---|---|
| 6,849,725 B2 * | 2/2005 | Junghans | C12N 15/117 536/23.1 |
| 9,499,815 B1 * | 11/2016 | Schroff | C12N 15/117 |

FOREIGN PATENT DOCUMENTS

| | | |
|---|---|---|
| WO | 2007/131495 A2 | 11/2007 |
| WO | 2015/124614 A1 | 8/2015 |

OTHER PUBLICATIONS

Fourcade et al, Cancer Res., vol. 74, No. 4, pp. 1045-1055 (Year: 2013).*
Duraiswamy et al. Cancer Res., vol. 73, No. 23, pp. 6900-6912 (Year: 2013).*
Sara Mangsbo, "Immunological Checkpoint Blockade and TLR Stimulation for Improved Cancer Therapy", Acta Universitatis Upsaliensis. Digital Comprehensive Summaries of Uppsala Dissertations from the Faculty of Medicine 506, Dec. 15, 2009, pp. 1-84, XP055275073.
Jaikumar Duraiswamy et al., "Therapeutic PD-1 Pathway Blockade Augments with Other Modalities of Immunotherapy T-Cell Function to Prevent Immune Decline in Ovarian Cancer", Cancer Research, Dec. 1, 2013, pp. 6900-6912, vol. 73, No. 23.
Julien Fourcade et al., "PD-1 and Tim-3 Regulate the Expansion of Tumor Antigen—Specific CD8+ T Cells Induced by Melanoma Vaccines", Cancer Research, Feb. 15, 2014, pp. 1045-1055, vol. 74, No. 5.
Raymond M. Wong et al., "TLR-9 signaling and TCR stimulation co-regulate CD8+ T cell-associated PD-1 expression", Immunology Letters, Dec. 2, 2009, pp. 60-67, vol. 127, No. 1.
Aurelien Marabelle et al., "Depleting tumor-specific Tregs at a single site eradicates disseminated tumors", Journal of Clinical Investigation, American Society for Clinical Investigation, Jun. 1, 2013, pp. 2447-2463, vol. 123, No. 6.
Luxembourg Search Report for LU 92821, dated May 25, 2016.
International Search Report for PCT/EP2016/071314, dated Feb. 16, 2017.

* cited by examiner

Primary Examiner — Jane J Zara
(74) Attorney, Agent, or Firm — Sughrue Mion, PLLC

(57) ABSTRACT

The invention relates to a combination and its use for the treatment of diseases. The instant disclosure provides a combination of a so-called T-cell regulator selected from the group comprising PD1, PD-L1, OX40, TIM-3, LAG3, CD137(4-1BB) and a non-coding immunomodulating DNA.

3 Claims, 13 Drawing Sheets
Specification includes a Sequence Listing.

SEQUENCE LISTING

```
<160> NUMBER OF SEQ ID NOS: 12

<210> SEQ ID NO 1
<211> LENGTH: 48
<212> TYPE: DNA
<213> ORGANISM: Artificial Sequence
<220> FEATURE:
<223> OTHER INFORMATION: synthetic oligodeoxynucleotide
```

```
<400> SEQUENCE: 1
gttcctggag acgttcttag gaacgttctc cttgacgttg gagagaac        48

<210> SEQ ID NO 2
<211> LENGTH: 60
<212> TYPE: DNA
<213> ORGANISM: Artificial Sequence
<220> FEATURE:
<223> OTHER INFORMATION: synthetic oligodeoxynucleotide

<400> SEQUENCE: 2
accttccttg tactaacgtt gcctcaagga aggttgatct tcataacgtt gcctagatca    60

<210> SEQ ID NO 3
<211> LENGTH: 18
<212> TYPE: DNA
<213> ORGANISM: Artificial Sequence
<220> FEATURE:
<223> OTHER INFORMATION: synthetic oligodeoxynucleotide

<400> SEQUENCE: 3
aacgttcttc ggggcgtt                                                  18

<210> SEQ ID NO 4
<211> LENGTH: 58
<212> TYPE: DNA
<213> ORGANISM: Artificial Sequence
<220> FEATURE:
<223> OTHER INFORMATION: synthetic oligodeoxynucleotide

<400> SEQUENCE: 4
aggtggtaac ccctaggggt taccaccttc atcgtcgttt tgtcgttttg tcgttctt      58

<210> SEQ ID NO 5
<211> LENGTH: 116
<212> TYPE: DNA
<213> ORGANISM: Artificial Sequence
<220> FEATURE:
<223> OTHER INFORMATION: synthetic oligodeoxynucleotide

<400> SEQUENCE: 5
cctaggggtt accaccttca ttggaaaacg ttcttcgggg cgttcttagg tggtaacccc    60
taggggttac caccttcatt ggaaaacgtt cttcggggcg ttcttaggtg gtaacc       116

<210> SEQ ID NO 6
<211> LENGTH: 58
<212> TYPE: DNA
<213> ORGANISM: Artificial Sequence
<220> FEATURE:
<223> OTHER INFORMATION: synthetic oligodeoxynuclotide

<400> SEQUENCE: 6
aggtggtaac ccctaggggt taccaccttc atcgtcgttt tgtcgttttg tcgttctt      58

<210> SEQ ID NO 7
<211> LENGTH: 33
<212> TYPE: DNA
<213> ORGANISM: Artificial Sequence
<220> FEATURE:
<223> OTHER INFORMATION: synthetic oligodeoxynucleotide; Position 31 and
      32 in L-conformation

<400> SEQUENCE: 7
ggggtcatta aaacgtgacg tgacgttctt ttt                                 33
```

```
<210> SEQ ID NO 8
<211> LENGTH: 37
<212> TYPE: DNA
<213> ORGANISM: Artificial Sequence
<220> FEATURE:
<223> OTHER INFORMATION: synthetic oligodeoxynucleotide; Positions 1, 2
      and 35 and 36 in L-conformation

<400> SEQUENCE: 8
ggggggggtc attaaaacgt gacgtgacgt tcttttt                                    37

<210> SEQ ID NO 9
<211> LENGTH: 32
<212> TYPE: DNA
<213> ORGANISM: Artificial Sequence
<220> FEATURE:
<223> OTHER INFORMATION: synthetic oligodeoxynucleotide; positions 30
      and 31 in L-conformation

<400> SEQUENCE: 9
ggggtcatta aacgtgacgt gacgttcttt tt                                         32

<210> SEQ ID NO 10
<211> LENGTH: 34
<212> TYPE: DNA
<213> ORGANISM: Artificial Sequence
<220> FEATURE:
<223> OTHER INFORMATION: synthetic oligodeoxynucleotide; positions 32
      and 33 in L-conformation

<400> SEQUENCE: 10
ggggtcatta aacgttcttc ggggcgttct tttt                                       34

<210> SEQ ID NO 11
<211> LENGTH: 39
<212> TYPE: DNA
<213> ORGANISM: Artificial Sequence
<220> FEATURE:
<223> OTHER INFORMATION: synthetic oligodeoxynucleotide; positions 37
      and 38 in L-conformation

<400> SEQUENCE: 11
ggggtcatta aatcgtcgtt ttgtcgtttt gtcgttttt                                  39

<210> SEQ ID NO 12
<211> LENGTH: 21
<212> TYPE: DNA
<213> ORGANISM: Artificial Sequence
<220> FEATURE:
<223> OTHER INFORMATION: synthetic oligodeoxynucleotide; positions 1, 2
      and 19 and 20 in L-conformation

<400> SEQUENCE: 12
gggggacgat cgtcgggggg t                                                     21
```

COMBINATION COMPRISING IMMUNOSTIMULATORY OLIGONUCLEOTIDES

CROSS REFERENCE TO RELATED APPLICATIONS

This application is a National Stage of International Application No. PCT/EP2016/071314 filed Sep. 9, 2016, claiming priority based on Luxembourg Patent Application No. 92821, filed Sep. 9, 2015.

FIELD OF THE INVENTION

The invention relates to a combination and its use for the treatment of diseases.

BRIEF DESCRIPTION OF THE RELATED ART

The term "immunotherapy" defines the treatment of diseases by stimulating, inducing, enhancing or suppressing an immune response. The strategy of immunotherapies is to fight diseases, such as cancer, infectious diseases, allergy and asthma.

A variety of active agents, so called immunomodulators, that can be used in immunotherapy are known. Most established immunomodulators belong to small molecules or nucleic acids, many of which interact with the toll-like receptor system. Most known immunomodifying short DNA sequences contain an unmethylated cytosine guanine motif (CG motif), which has been described by Krieg et al. (Nature 1995 374: 6522 546-549). The occurrence of unmethylated CG motifs is substantially suppressed in the genome of eukaryotes compared to prokaryotes or viruses. Therefore, DNA molecules containing such a motif have evolved as a natural "danger signal" and trigger the immune system in the fight against prokaryotic or viral pathogens. This can be exploited therapeutically or prophylactically by using such sequences to treat or prevent infectious diseases with immunotherapy. A particular emphasis has in recent years been put on the use of such immunomodulators in cancer therapy, with the aim of activating the patient's own immune system to fight against tumors.

DNA constructs comprising unmethylated CG motifs are able to elicit a considerable physiological effect by strongly stimulating effector cells of the innate immune system including dendritic cells, macrophages, natural killer (NK) and NKT cells. Unmethylated CG motifs are detected by the innate immune pattern recognition receptor Toll-like receptor (TLR) 9. While the exact recognition mechanism is not yet fully understood, significant progress in unraveling the underlying pathways has been made (A. Krieg, Nat. Rev. Drug Disc., 5:471-484, 2006).

It is assumed that upon binding of DNA constructs containing unmethylated CGs to the receptor, multiple signal cascades are activated in responding cells. By upregulation of characteristic surface molecules and secretion of cytokines, adaptive immunity with a predominant Th1 pattern is induced. Such constructs can be used in combination with, for example, antibodies, chemotherapy or radiation therapy, vaccines or cytokines. Allergic diseases and asthma are mostly Th2-mediated. By increasing the ratio of Th1/Th2, the Th2-mediated responses are attenuated and thereby these types of diseases can be treated or prevented.

Surface molecules, which are unregulated by the TLR-9 pathway, include, for example, CD40, CD69, CD80, CD86 or CD169, depending on the cell type. The enhanced secretion of cytokines is also characteristic for distinct cell types; cytokines include, for example, macrophage inflammatory proteins (MIP)-1alpha, MIP-1beta, interleukin (IL)-6, IL-8, interferon (IFN)-alpha, tumor necrosis factor (TNF)-alpha, IFN-gamma, monocyte chemotactic protein (MCP)-1 or IFN-gamma-induced protein of 10 kDa (IP-10).

In order to prevent or treat diseases, vaccination has been proven as a very effective approach. To ensure a strong and durable immune response, adjuvants capable of stimulating antigen-presenting cells such as dendritic cells, are usually administered together with the antigen, and for that purpose TLR9 agonists have been shown to be potent immunostimulants.

Preclinical and ongoing clinical studies support the use of TLR-9 agonists as immunomodulators and/or adjuvants, and prove their anti-tumor effect by enhancing both the humoral and cellular responses.

Independently of any explanations of the underlying mechanisms by which unmethylated CG motifs influence or modulate an immune response, many approaches were developed for modulation of the immune system by using such motifs. The WO 1998/018810 discloses that immunostimulatory sequences containing unmethylated CG motifs are even more effective when they are part of a single strand. However, administering an open-chained single-stranded DNA molecule is not practicable due to the quick degradation of single-stranded nucleic acids. Consequently, different methods for the protection of single- or double-stranded DNA constructs comprising an unmethylated CG motif were developed.

To achieve resistance against the degradation by DNA nucleases the phosphodiester bonds in the backbone of a nucleic acid polymer are frequently modified to phosphorothioates. Besides a somewhat less stimulatory activity of such phosphorothioate-protected nucleic acids clinical trials within the last years showed that the toxicity of a phosphorothioate-protection exclude or severely limit such nucleic acids from any use in pharmaceutical compositions or medicaments.

From the four classes of known activators with distinct immunomodulation profiles all members except two comprise linear DNA molecules. One exception is disclosed in EP 1 196 178. This document discloses short deoxyribonucleic acid molecules, comprising a partially single-stranded, dumbbell-shaped, covalently closed sequence of nucleotide residues comprising CG motifs ("dSLIM") consisting entirely of natural DNA. According to the disclosure of the EP 1 196 178 the CG motifs are located within the single-stranded loops at both ends of the double-stranded stem of the disclosed molecule or within the double-stranded stem. The single-stranded hairpin loops protect a double-stranded stem from degradation by DNA nucleases within or outside of the cell. GB 1402847.6 discloses a somewhat similar dumbbell structure utilizing a different sequence.

Another exception from linear oligonucleotides is disclosed in WO 2012/085291. This document teaches DNA constructs comprising nucleotides in L-conformation. According to the data disclosed in WO 2012/085291, the number of nucleotides in L-conformation and their position within the DNA construct influences the immunostimulatory capability of the DNA construct. A DNA construct comprising only nucleotides in L-conformation does for instance not efficiently stimulate the immune system.

Document WO 2010/039137 discloses immune regulatory oligonucleotides as antagonists for TLR mediated diseases having one or more chemical modifications in the sequence flanking an immune stimulatory motif and/or in an oligonucleotide motif that would be immune stimulatory but for the modification. Thus, the intention of the disclosed oligonucleotides of WO 2010/039137 is to suppress an immune response caused by TLRs.

WO 2005/042018 describes new so-called C-class CpG oligonucleotides, wherein a c-class oligonucleotide is characterised by CpG sequences, generally positioned at or near the 5' end or 3' end of the molecule, and a GC-rich palindrome motif, generally positioned at or near the other end of the molecule. The document discloses variations of the palindromic sequence of a c-class DNA.

Document WO 2015/124614 discloses covalently closed DNA construct, a pharmaceutical composition and a vaccine and their use for the modulation of the immune system, wherein the DNA construct comprises specific DNA sequences.

The strong stimulation of a cellular immune response makes it possible to influence regulatory circuits, and without such intervention no satisfactory immune activity would occur in the patient. This includes inducing a response to "weak" antigens, i.e. non-activating within MHC-I presentation, for example breakpoint peptides from chromosomal translocations or mutated oncogenes, often occurring in tumour diseases (Melief C J, Kast W M; T-cell immunotherapy of cancer; Res Immunol 1991 June-August; 142(5-6):425-9; also: Pasternak G, Hochhaus A, Schultheis B, Hehlmann R; Chronic myelogenous leukemia: molecular and cellular aspects; J Cancer Res Clin Oncol 1998; 124 (12):643-60). It may also be desirable to break the tolerance to autoantigens such as the tyrosinase or tyrosinhydroxylase expressed in tumour cells of malignant melanoma and represented in MHC-I. (Weber L W, Bowne W B, Wolchok J D, Srinivasan R, Qin J, Moroi Y, Clynes R, Song P, Lewis J J, Houghton A N; Tumor immunity and autoimmunity induced by immunization with homologous DNA; J Clin Invest 1998 Sep. 15; 102(6):1258-64; Surman D R, Irvine K R, Shulman E P, Allweis T M, Rosenberg S A, Restifo N J; Generation of polyclonal rabbit antisera to mouse melanoma associated antigens using gene gun immunization; Immunol Methods; 1998 May 1; 214(1-2):51-62).

Another, extremely important aspect is the adjuvant effect of ISS in prophylactic vaccinations as well as the possibility of re-polarizing the reaction of an existing infection from a type-2 response to a type-1 response, thus enabling the pathogen to be controlled (Kovarik J, et al. CpG oligodeoxynucleotides can circumvent the Th2 polarization of neonatal responses to vaccines but may fail to fully redirect Th2 responses established by neonatal priming; J Immunol. 1999 Feb. 1; 162(3):1611-7). It has been demonstrated for a large number of pathogens that the type of immune response has a decisive influence on the course of the infection or on the patient's ability to survive. As far as allergic reactions represent a type-2 overshoot response, ISS is expected to provide a therapeutic effect for indications of this kind as well.

It has been observed that certain sequences containing CpGs possess a characteristic which neutralises ISS-induced stimulation, i.e. that sequences of this kind are able to suppress the stimulatory effect of ISS when added to them (Krieg A M, Wu T, Weeratna R, Efler S M, Love-Homan L, Yang L, Yi A K, Short D, Davis H L; Sequence motifs in adenoviral DNA block immune activation by stimulatory CpG motifs; Proc Natl Acad Sci USA 1998 Oct. 13; 95(21): 12631-6). Without having fully explained the underlying mechanism of the effect of these sequence motifs described as neutralising CpG motifs ("CpG-N"), the authors of the publication quoted here imply that this effect is limited to blocking stimulation by ISS. As long as the mechanism of immune induction by ISS is not explained, one cannot rule out the possibility that these CpG-N motifs also possess other immunomodifying properties of therapeutical significance.

There is at least one human disease, systemic lupus erythematosus, which is characterized by the confirmed existence of anti-DNA antibodies in patient serum, and where it is suspected that a reaction to bacterial ISS has aetiological reasons (Krieg A M, CpG DNA: a pathogenic factor in systemic lupus erythematosus?, J Clin Immunol 1995 November; 15(6):284-92). In these cases and in other indications, blocking the underlying mechanisms using CpG-N motifs would be beneficial.

Independent of any explanation of the underlying mechanisms, the potential of CpG sequences for influencing the immune response is considerable and has generated sudden and widespread scientific interest in the phenomenon as well as in exploring the possibilities for therapeutic and prophylactic applications where infections, tumours and immune deficiencies are concerned.

The literature concerning ISS states (see e.g. WO09818810A1, p. 17, ll 29-30), and this is confirmed by the invention described (see below), that immunostimulatory sequences containing CpGs are more effective when they occur as single strands. Administering short, open-chain, single-strand ISS oligodeoxynucleotides with the objective of immune modification is the next logical step to take, and is the subject of numerous experimental approaches for treating infectious illnesses, tumours and autoimmune diseases. However, open-chain, single-strand oligodeoxynucleotides are degraded very quickly by extracellular and intracellular exonucleases and are therefore very difficult to use in in-vivo applications. The nucleases mentioned display considerably reduced enzymatic activity when compared to modified phospho-ester bonds in the backbone of nucleic acid polymers; this has led to phosphor thioesters ("thioates") or reduced phosphor bonds (phosphonates) in chiral or achiral form being used in applications where single-strand nucleic acid molecules are to be administered to the patient. These modified compounds can be produced by solid phase synthesis, yet to some extent only by considerably more complicated methods by comparison with classic DNA amidite synthesis. These compounds are known from antisense research; in clinical studies of antisense strategies, however, it was also demonstrated that they have considerable side effects, particularly on the blood coagulation system and complement system (see e.g. Sheehan and Lan, Blood 92, 1617-1625 (1998)). In connection with the use of thiophosphoric acid derivatives for nuclease protection of ISS it was also demonstrated that the sequences display less stimulatory activity when those cytosine-guanosine residues which are actually effective are themselves protected by the flanking sequences required for the activity itself (see WO 98/18810).

The teaching concerning use and production of immunostimulatory ISS containing CpGs is comprehensively described in WO 98/18810, as well as in the documents quoted therein. The necessity for protecting oligodeoxynucleotides from exonucleases is described in detail in WO 98/18810. A number of solutions are presented for solving the problem of insufficient in vivo stability, which are however expressly limited to single-strand linear ODNs; mention is made of thiophosphate esters, dithiophosphate esters or phosphonates. The possibility of stabilising the ODN by creating secondary structures, in particular a stem-loop, is noted in WO 98/18810. Production and use of phosphorothioate oligomers in connection with immunostimulatory sequences is described in U.S. Pat. Nos. 5,663,153, 5,723,335 as well as in U.S. Pat. No. 5,856,462.

A different strategy for protecting single-strand sequences is described in U.S. Pat. No. 5,750,669. Here the ends of the oligomers are linked with nucleoside residues connected by 5'-5' and 3'-3' bonds, which block exonucleolytic degradation.

Double stem-loop or covalently closed, dumbbell-shaped ODNs are known from experimental approaches in which competition in bonding sites for DNA binding proteins, as well as transcription factors were the focus of research (Lim et al. 1997, Nuc. Acids Res. 25, 575-581; Blumenfeld et al., Nuc. Acids Res. 1993, 21, 3405-3411).

The T cell response of the human immune system is regulated by multiple T-cell regulating molecules to avoid over-activation of the immune system on healthy cells (Pardoll D M. Nat Rev Cancer. 2012; 12(4):252-264; Sharma P, Wagner K, Wolchok J D, Allison J P. Nat Rev Cancer. 2011; 11(11):805-812). Such T-cell regulating molecules are summarized as "T-cell regulator" within the context of the instant disclosure and comprise checkpoint inhibitors and co-stimulants. Tumor cells often take advantage of these regulatory systems to escape detection by the immune system. Inhibition of a checkpoint of the immune system and co-stimulation of the T-cell system may enhance the anti-tumor immune response. The blockade of immune checkpoints and thus liberation of tumor-specific T cells to exert their effector function against tumor cells has demonstrated efficacy in cancer settings, and clinical trials are ongoing (Hodi F S, O'Day S J, McDermott D F, et al. N Engl J Med. 2010; 363(8):711-723; Robert C, Thomas L, Bondarenko I, et al. N Engl J Med. 2011; 364(26):2517-2526; Wolchok J D, H. Kluger, M. K. Callahan, et al. N Engl J Med, 369 (2013), pp. 122-133).

Cytotoxic T-lymphocyte antigen (CTLA)-4 and programmed cell death (PD)-1 represent two checkpoints, which have been studied most extensively as targets for cancer therapy so far. CTLA-4 is a potent co-inhibitor that has been shown to be aberrantly upregulated on the surface of T cells in certain cancers. It decreases T-cell activation in response to tumor cells and is thus involved in early T-lymphocyte tolerance. PD-1 has been found to be upregulated in certain tumors, inhibiting T-cell function helping the tumor to evade the immune system by playing a role in maintaining peripheral T-lymphocyte tolerance (Keir M E, Butte M J, Freeman G J, Sharpe A H, et al. Annu Rev Immunol. 2008; 26:677-704; Mahoney K M, Freeman G J, McDermott D F. Clinical Therapeutics 37(4): 764-782, 2015).

The first immune-checkpoint inhibitor approved by the US Food and Drug Administration (FDA) in 2011 was ipilimumab, a monoclonal antibody that blocks CTLA-4 for the treatment of metastatic melanoma. Blocking the interaction between PD-1 and one of its ligands, PD-L1 (also known at B7-H1 and CD274), has been reported to generate antitumor responses (Pardoll D M. Nat Rev Cancer. 2012; 12(4):252-264).

Another inhibitory molecule, lymphocyte activation gene-3 (LAG-3), a CD4 homolog that binds to MHC class II molecules, is expressed on activated T cells, B cells, NK cells, and tumor-infiltrating lymphocytes, and is thought to negatively regulate T-cell expansion by limiting T-cell activation (Pardoll D M. Nat Rev Cancer. 2012; 12(4):252-264; Goldberg M V, Drake C G. Curr Top Microbiol Immunol 2011; 344:269-78). Its blockade augments T cell proliferation and enhances anti-tumor T cell responses (Nguyen L T, *Nat Rev Immunol,* 2015).

Further, T-cell immunoglobulin mucin-3 (TIM-3), the ligand of which is galectin 9 (upregulated in various types of cancer), is expressed by IFN-secreting helper T (TH 1) cells, as well as dendritic cells, monocytes, and T cells [Ngiow S F, Teng M W, Smyth M J. Cancer Res. 2011; 71(20:6567-71]. It inhibits T helper 1 cell responses, and TIM-3 antibodies enhance antitumor immunity (Anderson A C. Curr Opin Immunol 2012; 24:213-6). When bound to its ligand, galectin-9, TIM-3 induces TH1 cell death (Zhu C, Anderson A C, Schubart A, et al. Nat Immunol. 2005; 6(12):1245-52). Studies of TIM-3-deficient mice suggest that the TIM-3 pathway inhibits the expansion and effector functions of TH 1 cells and may be important for tolerance induction of TH1 cells (Sabatos C A, Chakravarti S, Cha E, et al. Nat Immunol. 2003; 4(11):1102-10). TIM-3 has also been reported to be co-expressed with PD-1 on tumor-specific CD8+ T cells, and dual blockade of both molecules significantly enhances the in vitro proliferation and cytokine production of human T cells. In animal models, coordinate blockade of PD-1 and TIM-3 was reported to enhance anti-tumor immune responses and tumor rejection (Pardoll D M. Nat Rev Cancer. 2012; 12(4):252-264).

B- and T-lymphocyte attenuator (BTLA/CD272) was identified as an inhibitory receptor on T cells and. HVEM/TNFRSF14—which is expressed on tumor cells as well as on tumor-associated endothelial cells—was shown to be the BTLA ligand. BTLA expression levels are high on tumor infiltrating lymphocytes (TIL) from patients with melanoma and BTLA-expressing T cells are inhibited in the presence of its ligand, HVEM. BTLA can inhibit the function of tumor-specific human CD8$^+$ T cells (Paulos C M, June C H. J Clin Invest 2010; 120:76-80). Thus, BTLA may also be a relevant inhibitory receptor for T cells in the tumour microenvironment and a target for checkpoint inhibition strategies (Pardoll D M. Nat Rev Cancer. 2012; 12(4):252-264).

OX40 (CD134/TNFRSF4) is a member of the TNFR super-family and is expressed by CD4 and CD8 T cells during antigen-specific priming. Ligation of OX40 on CD8 and CD4 T cells promotes their survival and expansion. Furthermore activating OX40 boosts the generation of tumor-reactive effector T cells and inhibits T-cell function. Preclinical studies demonstrated that treatment of tumor-bearing hosts with OX40 agonists resulted in tumor regression in several preclinical models (Linch S N, McNamara M J, Redmond W L. Front Oncol. 2015 5:34).

The co-stimulatory receptor CD137 (4-1BB/TNFSF9) possesses an unequaled capacity for both activation and pro-inflammatory polarization of anti-tumor lymphocytes. Co-stimulation through the CD137/4-1BB receptor activates multiple signaling cascades within the T cell, powerfully augmenting T cell activation. Stimulation of CD137 on antigen-primed T-lymphocytes increase tumor immunity and CD137 monotherapy is capable of mediating significant tumor regressions and even cures of numerous types of established murine tumors (Bartkowiak T, Curran M A. Front Oncol. 2015 5:117).

Based on this state of the art, the objective of the instant disclosure is to provide an efficient combination comprising immunostimulatory DNA constructs and its use as a medicament.

SUMMARY OF THE INVENTION

With regard to the prior art it is an objective of the instant disclosure to provide a combination of molecule binding to a T-cell regulator and an immunomodulating DNA construct in form of a non-coding sequence of deoxyribonucleotides.

The present disclosure teaches a combination comprising the components of a chemical or molecule binding to at least one of the molecules selected from the group comprising PD1, PD-L1, OX40, TIM-3, LAG3, CD137(4-1BB) for affecting their function as checkpoint inhibitors or co-stimulants; and a non-coding sequence of deoxyribonucleic acids comprising at least one sequence motif $N^1N^2CGN^3N^4$, wherein N is a nucleotide comprising A, C, T, or G, and C is deoxycytidine, G is deoxyguanosine, A is deoxyadenosine and T is deoxythymidine.

The molecule binding to a T-cell regulator may be a protein or peptide, like an antibody, which is synthetically or biologically manufactured.

The combination of the instant disclosure may comprise for $N^1N^2$ an element taken from the group of GT, GG, GA, AT and AA, and for $N^3N^4$ an element taken from the group of CT, TG and TT.

The non-coding sequence of deoxyribonucleic acids may either be linear open-chained on both sides, linear open-chained on one side of a double stranded part with a single stranded hairpin on the respective other side of the double strand or a dumbbell-shaped partially single-stranded covalently closed chain of deoxyribonucleic acids.

The combination may further comprise at least three of said sequence motifs $N^1N^2CGN^3N^4$.

It is intended for a linear open-chained non-coding sequence of deoxyribonucleic acids that it may comprise at least one nucleotide in L-conformation, wherein one of the five terminal nucleotides located at the 5'- and/or the 3'-end of a DNA single strand of the linear open-chained non-coding sequence of deoxyribonucleic acids may be in L-conformation.

The combination of the instant disclosure may further comprise at least one of the following non-coding sequences of deoxyribonucleotides

```
a.
                                           (SEQ ID NO: 1)
GTTCCTGGAG ACGTTCTTAG GAACGTTCTC CTTGACGTTG
GAGAGAAC;
or b.
                                           (SEQ ID NO: 2)
ACCTTCCTTG TACTAACGTT GCCTCAAGGA AGGTTGATCT
TCATAACGTT GCCTAGATCA,
or c.
                                           (SEQ ID NO: 3)
AACGTTCTTCGGGG CGTT,
or d.
                                           (SEQ ID NO: 4)
AGGTGGTAAC CCCTAGGGGT TACCACCTTC ATCGTCGTTT
TGTCGTTTTG TCGTTCTT.
```

The combination may further comprise a non-coding sequence of deoxyribonucleic acids with a length of 40 to 200 nucleotides or of 48 to 116 nucleotides.

It is further intended that the sequence AACGTTCT-TCGGGG CGTT (SEQ ID NO:3) may be part of the sequence CCTAGGGGTT ACCACCTTCA TTG-GAAAACG TTCTTCGGGG CGTTCTTAGG TGG-TAACC CCTAGGGGTT ACCACCTTCA TTG-GAAAACG TTCTTCGGGG CGTTCTTAGG TGGTAACC (SEQ ID NO:5).

The sequence motif $N^1N^2CGN^3N^4$ can be part of a single stranded region of a non-coding sequence of deoxyribonucleotides, which is part of a combination according to the instant disclosure.

The combination may provide the components of both groups in a solid, liquid or gaseous form to be applied with maximal 15 mg/kg weight. This means that the dosage can be adapted to the weight of the organism to which the combination should be applied.

A method comprising the step of providing the components of a combination of the instant disclosure simultaneously, alternating or successively is another object of the invention. The non-coding sequence of deoxyribonucleic acids may be provided prior to the chemical or molecule for affecting the T-cell regulator or vice versa.

A further object of the instant disclosure is the use of the disclosed combination as a medicament or for the treatment of diseases like cancer, autoimmune diseases and inflammation.

The compounds of the disclosed combination may be administered simultaneously, alternating or successively for the treatment of cancer, autoimmune diseases and inflammation.

A use of the disclosed combination for the manufacture of a pharmaceutical or pharmaceutically preparation, including vaccines, comprising acceptable pharmaceutical salts is a further object of the instant invention. The pharmaceutical may release the compounds of the disclosed combination simultaneously, alternating or successively.

Finally, the use of a combination of the instant disclosure as an adjuvant in therapeutic or prophylactic vaccination is an object of the instant disclosure.

BRIEF DESCRIPTION OF THE FIGURES

The invention will be described on the basis of figures. It will be understood that the embodiments and aspects of the invention described in the figures are only examples and do not limit the protective scope of the claims in any way. The invention is defined by the claims and their equivalents. It will be understood by the skilled artisan that features of one aspect or embodiment of the invention can be combined with a feature of a different aspect or aspects of other embodiments of the invention. It shows:

DETAILED DESCRIPTION OF THE INVENTION

Figure 1A:
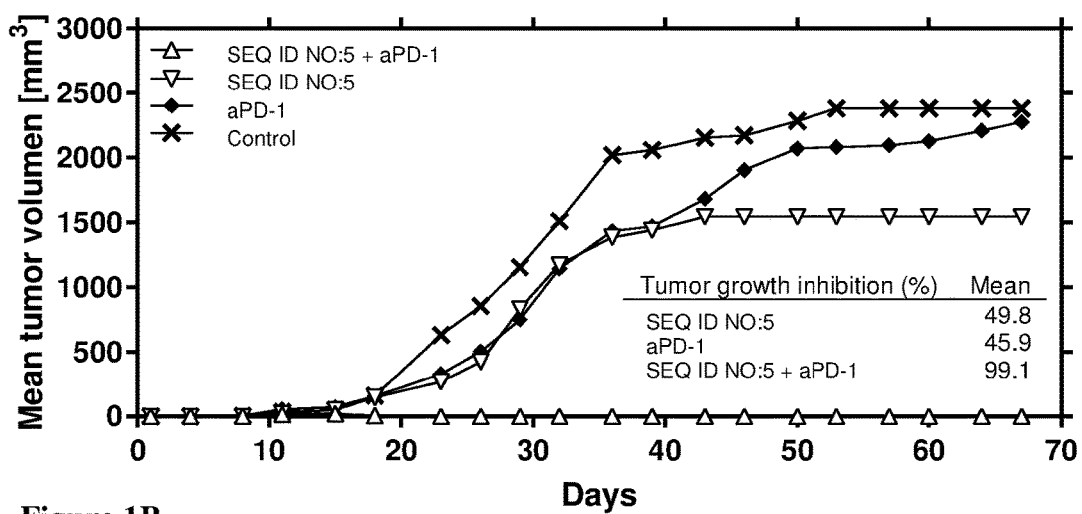
FIG. 1A, B Anti-tumor activity of the combination of SEQ ID NO:5 with anti-PD-1.

The instant invention provides a combination of a molecule binding to a so called T-cell regulator and a non coding sequence of deoxyribonucleic acids.

Within the meaning of the present disclosure a linear open-chained DNA sequence is designated as oligonucleotide, abbreviated with ODN. Said DNA sequence can be single-stranded or partially or completely double-stranded. The terms oligo, oligonucleotide and oligodeoxynucleotide are used synonymously and do not indicate a limitation of the length of the corresponding DNA sequence. The single components of oligonucleotides are nucleotides.

An oligo can be manufactured synthetically or be partially or completely of biological origin, wherein a biological origin includes genetically based methods of manufacture of DNA sequences.

L-DNA or nucleotides in L-conformation refer to nucleotides, which comprises L-deoxyribose as the sugar residue instead of the naturally occurring D-deoxyribose. L-deoxyribose is the enantiomer (mirror-image) of D-deoxyribose. Oligonucleotides partially or completely consisting of nucleotides in L-conformation can be partially or completely single- or double-stranded; however, nucleotides in L-conformation cannot hybridize to nucleotides in D-conformation (Hauser et al., Nucleic Acid Res. 2006 34: 5101-11). L-DNA is equally soluble and selective as D-DNA. Yet, L-DNA is resistant towards enzymatic exoactivity of naturally occurring enzymes, especially exonucleases, so L-DNA is protected against intracellular degradation (Urata et al., Nucleic Acids Res. 1992 20: 3325-32). Therefore, L-DNA is very widely applicable.

A "stem" according to the present disclosure shall be understood as a DNA double strand formed by base pairing either within the same oligonucleotide (which is then partially self-complementary) or within different oligonucleotides (which are partially or completely complementary). Intramolecular base-pairing designates base-pairing within the same oligonucleotide and base-pairing between different oligonucleotides is termed as intermolecular base-pairing.

A "loop" within the meaning of the present disclosure shall be understood as an unpaired, single-stranded region either within or at the end of a stem structure. A "hairpin" is a distinct combination of a stem and a loop, which occurs when two self-complementary regions of the same oligonucleotide hybridize to form a stem with an unpaired loop at one end.

A "solid phase" to which the nucleotides are covalently or non-covalently attached refers to, but is not restricted to, a column, a matrix, beads, glass including modified or functionalized glass, silica or silica-based materials including silicon and modified silicon, plastics (comprising polypropylene, polyethylene, polystyrene and copolymers of styrene and other materials, acrylics, polybutylene, polyurethanes etc.), nylon or nitrocellulose, resins, polysaccharides, carbon as well as inorganic glasses and plastics. Thus, microtiter plates are also within the scope of a solid phase according to the present disclosure.

Immunomodulation according to the present disclosure refers to immunostimulation and immunosuppression. Immunostimulation means preferentially that effector cells of the immune system are stimulated in order to proliferate, migrate, differentiate or become active in any other form. B cell proliferation for instance can be induced without co-stimulatory signals by immunostimulatory oligonucleotides, which normally require a co-stimulatory signal from helper thymocytes.

Immunosuppression on the other hand shall be understood as reducing the activation or efficacy of the immune system. Immunosuppression is generally deliberately induced to prevent for instance the rejection of a transplanted organ, to treat graft-versus-host disease after a bone marrow transplant, or for the treatment of autoimmune diseases such as, for example, rheumatoid arthritis or Crohn's disease.

In this context, immunomodulation may also refer to the influence of the nature or the character of an immune reaction, either by affecting or modifying an immune reaction, which is still developing or maturing or by modulating the character of an established immune reaction. Thus, affecting means in the context of checkpoint inhibitors to suppress their inhibitory effect, and in the context of co-stimulatory molecules to activate them.

The term "cancer" comprises cancerous diseases or a tumor being treated or prevented that is selected from the group comprising mammary carcinomas, melanoma, skin neoplasms, gastrointestinal tumors, including colon carcinomas, stomach carcinomas, pancreas carcinomas, colon cancer, small intestine cancer, ovarial carcinomas, cervical carcinomas, lung cancer, prostate cancer, kidney cell carcinomas and/or liver metastases.

Autoimmune diseases according to the present disclosure comprise rheumatoid arthritis, Crohn's disease, systemic lupus (SLE), autoimmune thyroiditis, Hashimoto's thyroiditis, multiple sclerosis, Graves' disease, myasthenia gravis, celiac disease and Addison's disease.

An agonist within the meaning of the instant disclosure and in accordance with its common definition represents a chemical or molecule that binds to another molecule, like a receptor or ligand and thus activates the molecule. In contrast to an agonist that activates, an antagonist shall be understood as a chemical or molecule that blocks the interaction of the molecule to which the antagonist binds with a respective agonist. Depending on the context, an antagonist in the understanding of the instant invention may also result in the activation of a process, because the antagonist blocks the interaction of another antagonist with a receptor for instance.

The term "pharmaceutically applicable or acceptable salts" as used herein includes salts of a compound of the combination, which are prepared with relatively nontoxic (i.e. pharmaceutically acceptable) acids or bases, depending on the particular substituents found on the compounds of the present invention. If, for example, compounds of the present invention contain acidic functionalities, base addition salts may be obtained by contacting the neutral form of such compounds with a sufficient amount of the desired base, either neat or in a suitable inert solvent. Non-limiting examples of pharmaceutically acceptable base addition salts include sodium, potassium, calcium, ammonium, organic amino, or magnesium salt, or a similar salt. If compounds of the present invention contain basic functionalities, acid addition salts may be obtained by contacting the neutral form of such compounds with a sufficient amount of the desired acid, either neat or in a suitable inert solvent. Non-limiting examples of pharmaceutically acceptable acid addition salts include those derived from inorganic acids like hydrochloric, hydrobromic, nitric, carbonic, phosphoric, partially neutralized phosphoric acids, sulfuric, partially neutralized sulfuric, hydroiodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention may contain both basic and acidic functionalities that allow the compounds to be converted into either base or acid addition salts. Contacting the salt with a base may regenerate the neutral forms of the compounds of the present invention or acid and isolating the parent compound in the conventional manner. The parent form of the compound differs from the various salt forms in certain physical properties, such as solubility in polar solvents, but otherwise the salts are equivalent to the parent form of the compound for the purposes of the present invention. The compounds of the present invention may possess chiral or asymmetric carbon atoms (optical centers) and/or double bonds. The racemates, diastereomers, geometric isomers and individual optical isomers are encompassed by the present invention. The compounds of the present invention may exist in unsolvated forms as well as solvated forms, including hydrated forms. In general, the solvated forms are equivalent to unsolvated forms and are also encompassed by the present invention. The compounds of the present invention may furthermore exist in multiple crystalline or amorphous forms.

Deoxyribonucleic acid molecules, consisting of a partially single-stranded, dumbbell-shaped, covalently closed chain of deoxyribonucleoside residues, which contain one or more sequences of the base sequence $N^1N^2CGN^3N^4$, wherein $N^1N^2$ is an element from the GT, GG, GA, AT or AA group, $N^3N^4$ is an element from the CT or TT group, as well as C deoxycytosine, G deoxyguanosine, A deoxyadenosine and T deoxythymidine, are used in combination with chemicals or molecules able to bind T-cell regulator of the immune system for immunostimulation in humans or higher animals.

The deoxyribonucleic acid molecules relating to the instant disclosure may have a length of up to 200 nucleotides. In particular, sequences with a length between 48 and 116 nucleotide are intended.

The dumbbell-shaped non-coding sequences of deoxyribonucleic acid molecules may comprise the base sequence $N^1N^2CGN^3N^4$ is their single-stranded regions.

The immunostimulation may take place in vitro or in vivo.

The instant disclosure provides also linear open-chained DNA sequence comprising at least one CpG motif and at least one nucleotide in L-conformation. Due to the partial/ complete L-conformation, the DNA sequence has no 5'- or 3'-ends that are accessible to exonucleases. In case that the construct has on one end of a double strand a single stranded-loop, the end is also protected against degradation. Thereby, the ODNs are in total protected against cellular degradation without having the need to use a phosphorothioate backbone, which has been shown to be toxic. In addition, the ODNs only consist of a minimum number of nucleotides, which makes them small and thereby easy to transfect into cells.

The non-coding sequence of ddeoxyribonucleic acids comprising at least one sequence motif $N^1N^2CGN^3N^4$ can be single-stranded or partially or completely double-stranded. This includes base-pairing within the same molecule (intramolecular) or within different molecules (intermolecular) or any combination thereof. It is also possible that the construct comprises at least one unpaired, single-stranded region. As a further embodiment, hairpin structures are included. Due to the partial or complete L-conformation, a longer half-life of the construct is ensured as nucleotides in L-conformation are not subject to degradation.

It is also within the scope of the instant disclosure that at least two molecules, which are single-stranded or partially or completely double-stranded can ligate to each other to form multimeric constructs. These multimeric constructs thus incorporate at least as many CpG motifs as ligation partners, tightly packed within one molecule, and are therefore expected to elicit also a considerable immune response as part of the combination with T-cell regulators. The resulting single-stranded or partially or completely double-stranded multimeric constructs can either be covalently closed comprising nucleotides in L-conformation within the molecule or open multimeric constructs comprising nucleotides in L-conformation at the 5'- and/or the 3'-end for protection against cellular degradation.

The disclosure further comprises chemical modifications of at least one nucleotide in the non-coding sequence of deoxyribonucleic acids comprising at least one sequence motif $N^1N^2CGN^3N^4$ with a functional group selected from the group comprising carboxyl, amine, amide, aldimine, ketal, acetal, ester, ether, disulfide, thiol and aldehyde groups. This allows coupling of the DNA construct to a compound selected from the group comprising peptides, proteins, carbohydrates, antibodies, synthetic molecules, polymers, micro projectiles, metal particles or a solid phase by, for example, adsorption, covalent or ionic bonding.

The modification can be specifically selected for the respective purpose. The construct can thus be used, for example, to shuttle other molecules to the specific cell responding to the CpG motif/s incorporated. In addition, it is possible by such modifications to couple the construct to micro projectiles, which can be used to transfer the construct into the cell. The construct can also be coupled to a solid phase, e.g. a microtiter plate.

Experiments described below were performed to investigate the influence of combining non-coding sequences of deoxyribonucleic acids with T-cell regulators. The experiments were conducted using dumbbell-shaped comprising the sequence motif $N^1N^2CGN^3N^4$, linear open-chained non-coding sequence of deoxyribonucleic acids comprising $N^1N^2CGN^3N^4$, wherein those constructs comprise nucleotides in L-conformation to prevent them from degradation. In addition, the effect of combining T-cell regulators with a non-coding sequence of deoxyribonucleic acids comprising $N^1N^2CGN^3N^4$ and twice the sequence of SEQ ID NO:4 were be investigated.

T-cell regulators antibodies binding to PD1, PD-L1, OX40, LAG-3, TIM3 and CD137(4-1BB) were used in a mouse model with injected human tumors. The effect on therapy after a growth phase is described in more detail below on growth of tumors in comparison to control groups.

The experiments compare dosage regimen with simultaneous, alternating or successive application of the components of the combination of the instant disclosure. In addition to the qualitative application of the compounds it was investigated whether reduced amounts of T-cell regulator are necessary for achieving comparable or even better results in applying the checkpoint inhibitor without a non-coding DNA sequence comprising a $N^1N^2CGN^3N^4$ sequence motif.

The in vitro analysis of the combinatory potential of TLR9 agonists with molecules binding to T-cell regulators comprises the use of in vitro cell culture system of human PBMC for evaluation of their T cells responses after stimulation. Stimulation of PBMC will be achieved with a mixture of immunogenic peptides from CMV, EBV, influenza and tetanus-toxin in the presence of antibodies against immunological T-cell regulators (e.g. PD-1, PD-L1, etc.) and TLR9 agonists (i.e. SEQ ID NO:5, SEQ ID NO:7, SEQ ID NO:10, SEQ ID NO:6).

The quantification of cytokines (IL-2 and IFN-gamma) in cell culture supernatants was determined. Although this in vitro cell culture system cannot mirror the complex interactions of immune cells in vivo, it provides evidences for an advantage of the combination of those TLR9 agonists.

DETAILED DESCRIPTION OF THE FIGURES

The combination of SEQ ID NO:5 with anti-PD-1 showed a surprisingly vastly increased anti-tumor effect compared to either anti-PD-1 or SEQ ID NO:5 monotherapy in a mouse A20 tumor model.

Figure 1B:
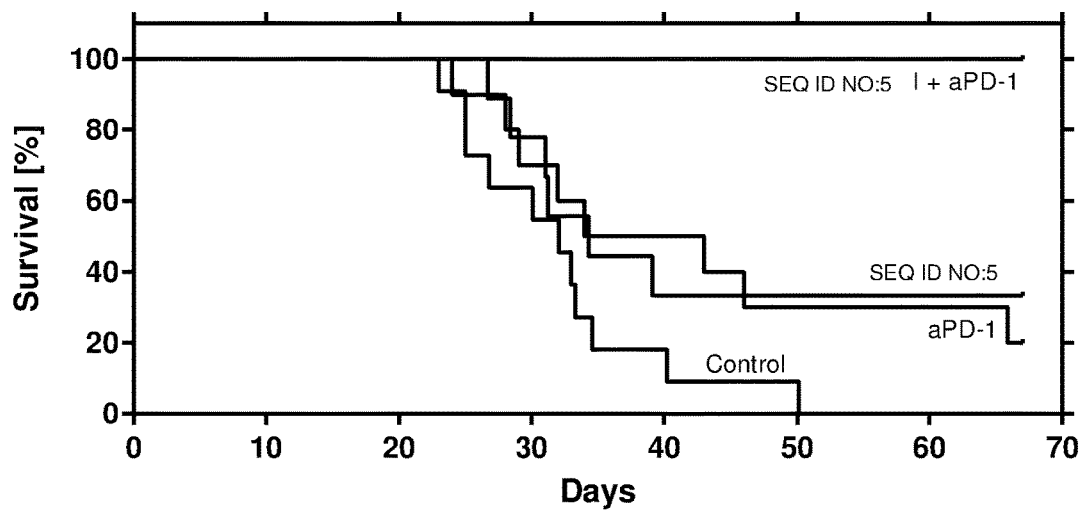

Tumor growth was surprisingly nearly completely inhibited by the combination of SEQ ID NO:5 and PD-1 (FIG. 1A, B). 9-12 mice per group were inoculated s.c. with A20 murine tumor cells and injected with SEQ ID NO:5 (250 µg/application, i.tu. on day 14, 16, 19, 21, 23, 26, 28, 30, 33 and 35), anti-PD-1 (100 µg/application i.p. on day 8, 11, 16 and 19), or both. Injection of vehicle (i.tu.) served as control. FIG. 1A shows the mean tumor growth—inlay, mean tumor growth inhibition from day 18 to 32 (at day 29: 46.0% for SEQ ID NO:5, 54.2% for anti-PD-1, 99.9% for the combination). FIG. 1B shows a Kaplan-Meier survival plot.

Figure 2:
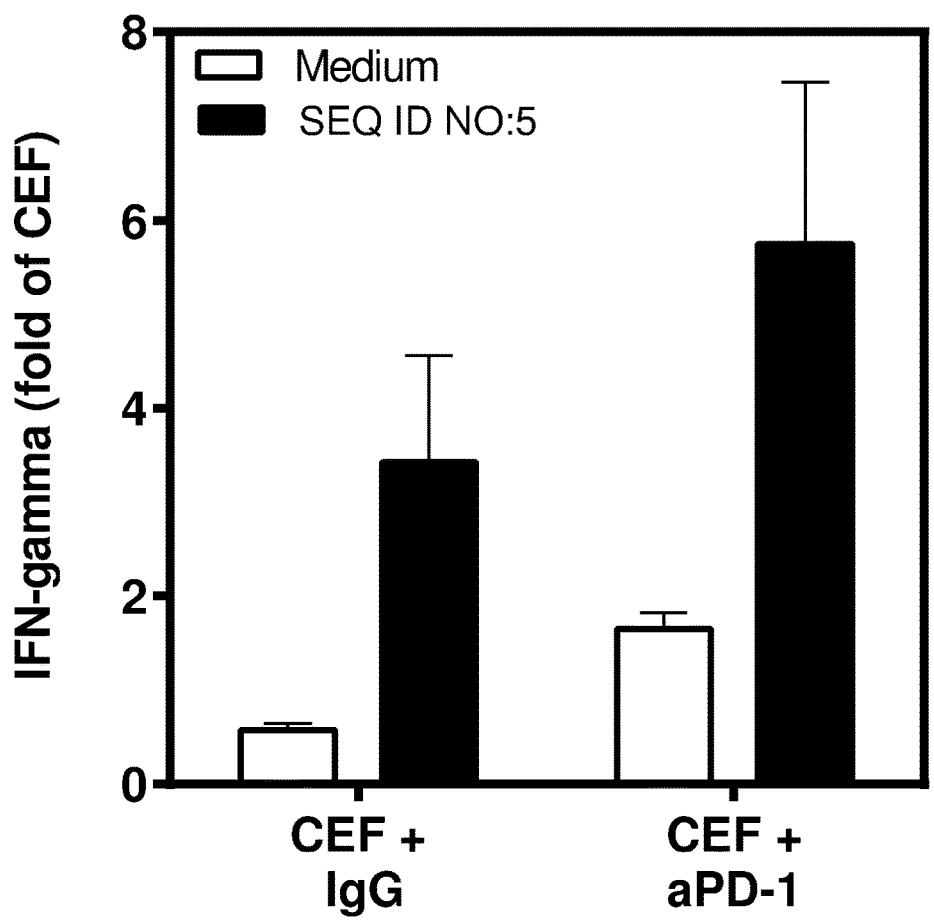
FIG. 2 In vitro stimulation of human PBMC with peptides selected from HLA class I-restricted T-cell epitopes of recall-antigens.

The synergistic combinatory effect of SEQ ID NO:5 with anti-PD-1 shown in FIG. 1 A, B was confirmed in vitro when human peripheral blood mononuclear cells (PBMC) were incubated with antigenic peptides and a combination of SEQ ID NO:5 and anti-PD-1. Peptides were selected from HLA class-I-restricted T-cell epitopes of recall antigens (CMV, EBV, Flu=CEF) and the combination with SEQ ID NO:5 clearly increased the INF-gamma secretion by the PBMC compared to injection of SEQ ID NO:5 or anti-PD-1 alone (FIG. 2). The final concentration of the peptides was 1 µg/ml per peptide, SEQ ID NO:5 was used in a concentration of 3 µM and anti-PD-1 with 10 µg/ml (n=4). IFN-gamma secretion was analyzed as a marker for immune response; normalized to IFN-gamma level after stimulation of PBMC with CEF-peptides alone. Murine IgG (10 µg/ml) was used as control for anti-PD-1.

Figure 3A:
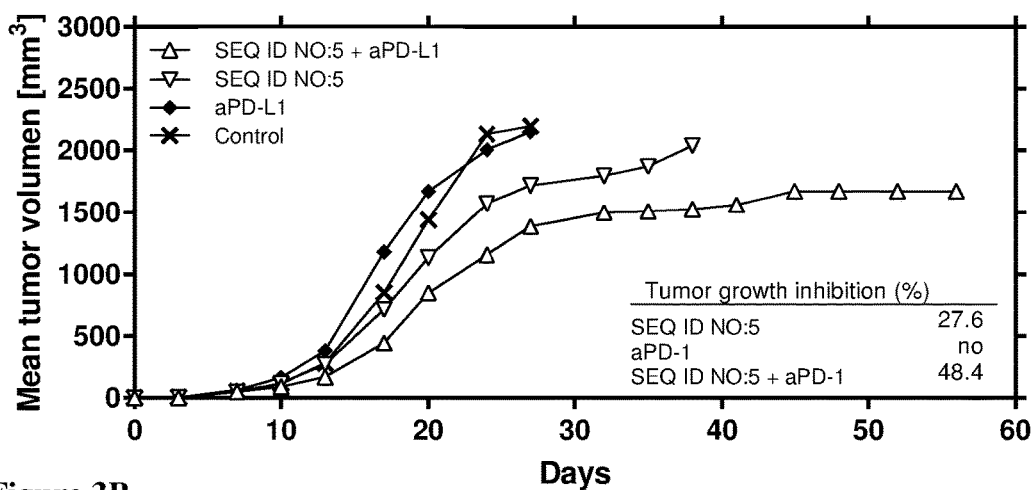
FIG. 3A, B Anti-tumor activity of the combination of SEQ ID NO:5 with anti-PD-L1.
Figure 3B:
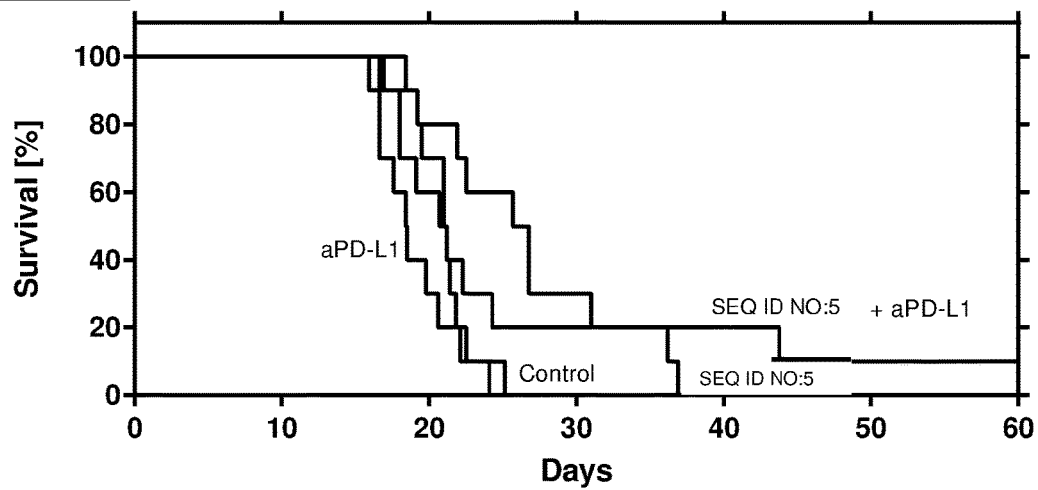

Furthermore, in a mouse CT26 tumor model, the surprising beneficial effects of the combination therapy of anti-PD-L1 and SEQ ID NO:5 was also clearly superior to the either SEQ ID NO:5 or anti-PD-L1 monotherapy. Tumor growth was reduced (FIG. 3A) and survival was augmented (FIG. 3B). 10 mice per group were inoculated s.c. with CT26 murine tumor cells and injected with SEQ ID NO:5 (250 µg/application, s.c. on day 3, 5, 7, 10, 12, 14, 17, 19, 21, 24, and 26), anti-PD-L1 (10 mg/kg per application, i.p. on day 3, 5, 7, 9, 11, 13, 15, 17), or both. Injection of vehicle (s.c.) served as control. FIG. 3A schows mean tumor growth—inlay, mean tumor growth inhibition from day 17 to 27 (at day 20: 23.0% for lefitolimod, no inhibition for anti-PD-L1, 39.9% for the combination). FIG. 1B shows a Kaplan-Meier survival plot.

The combinatorial effect of applying SEQ ID NO:6 having the the loop sequence TCATCGTCGTTTT-GTCGTTTTGTCGTTCTT was also investigated.

Figure 4A:
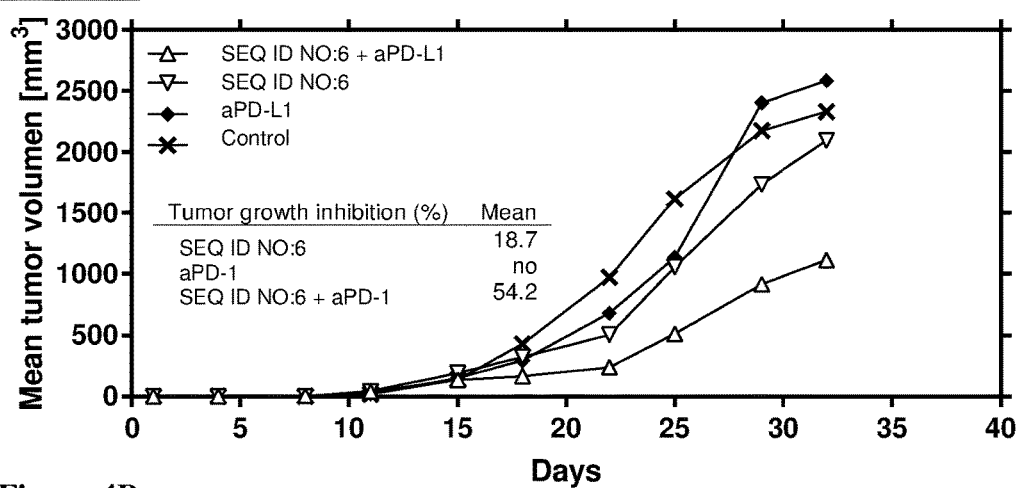
FIG. 4A, B Anti-tumor activity of the combination of SEQ ID NO:6 with anti-PD-1.

SEQ ID NO:6 was administered together with anti-PD-1 in a mouse CT26 tumor model. This combination surprisingly profoundly augmented the anti-tumor effect compared to the monotherapy with the single agents, SEQ ID NO:6 or anti-PD-1 (FIG. 4A, B). Again, 10 mice per group were inoculated s.c. with CT26 murine tumor cells and injected with SEQ ID NO:6 (250 µg/application, i.tu. on day 15, 17, 19, 22, 24, 26, 29, 31), anti-PD-1 (100 µg/application, i.p. on day 3, 6, 10 and 13), or both. Injection of vehicle (i.tu.) served as control. FIG. 4A shows the mean tumor growth—inlay, mean tumor growth inhibition from day 15 to 29 (at day 23: 48.2% for SEQ ID NO:6, no inhibition for anti-PD-1, 75.4 for the combination). FIG. 1B shows a mean Kaplan-Meier survival plot.

Figure 4B:
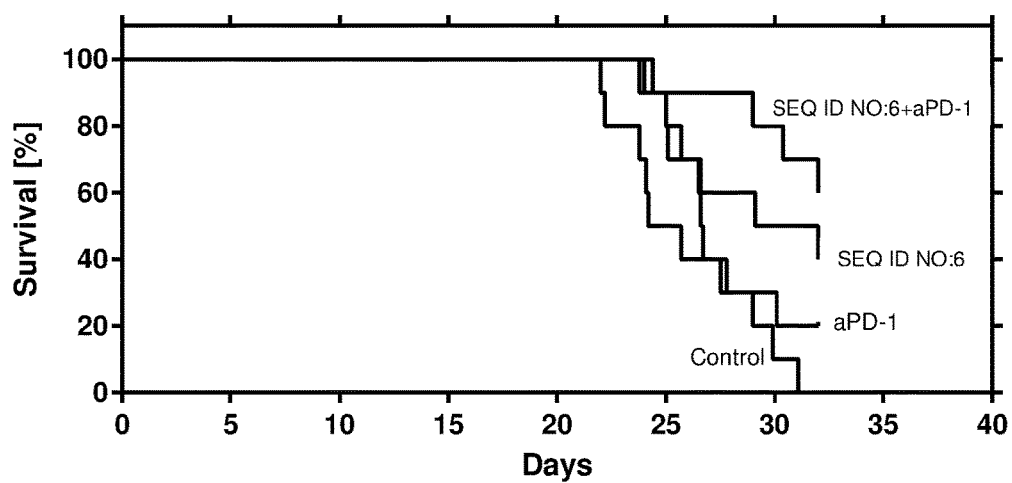
Figure 5:
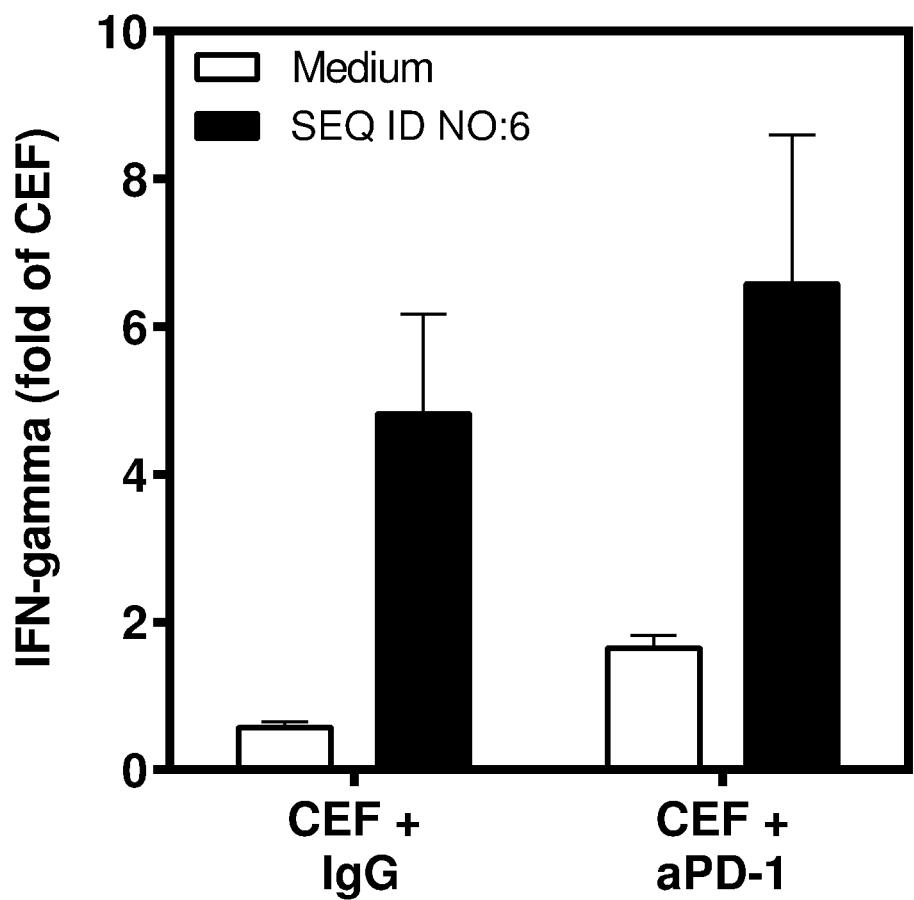
FIG. 5 In vitro stimulation of human PBMC with peptides selected from HLA class I-restricted T-cell epitopes of recall-antigens, SEQ ID NO:6 and anti-PD-1.

The results shown in FIG. 4 are in line with the in vitro stimulation data of human PBMC with antigenic peptides, also showing surprisingly a benefit of the combination over the single use of the compounds (FIG. 5). Peptides selected from HLA class I-restricted T-cell epitopes of recall-antigens (CMV, EBV, Flu=CEF) with a final concentration of 1 µg/ml per peptide, SEQ ID NO:6 in a concentration of 3 µM and anti-PD-1 with 10 µg/ml (n=4) were used. IFN-gamma secretion was used as a marker for immune response; normalized to IFN-gamma level after stimulation of PMBC with CEF-peptides alone. Murine IgG (10 µg/ml) was used as control for anti-PD-1.

Oligos comprising nucleotides in L-conformation were used in further studies. Those oligos comprise L-nucleotides at indicated positions. DNA molecules were used with the core sequence [yTCATTxCGTGACGTGACGTTCzv] (y=2 to 8 G, protected with 1 to 3 L-deoxyribose or not; x=3 to 4 A; z=2 to 6 T protected with 1 to 3 L-deoxyribose; v=A, G, C, T).

Figure 6A:
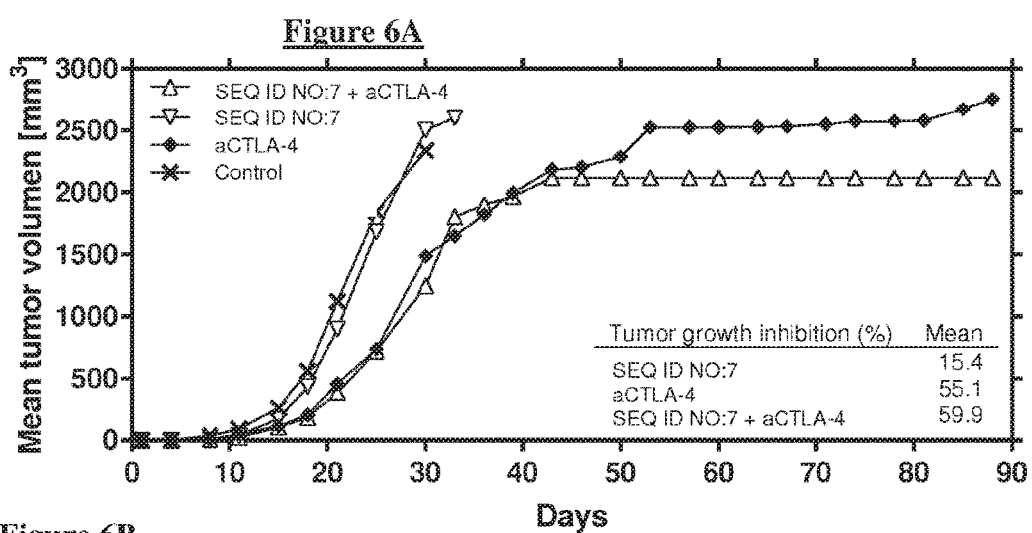
FIG. 6A, B Anti-tumor activity of the combination of SEQ ID NO:7 with anti-CTLA-4.
Figure 6B:
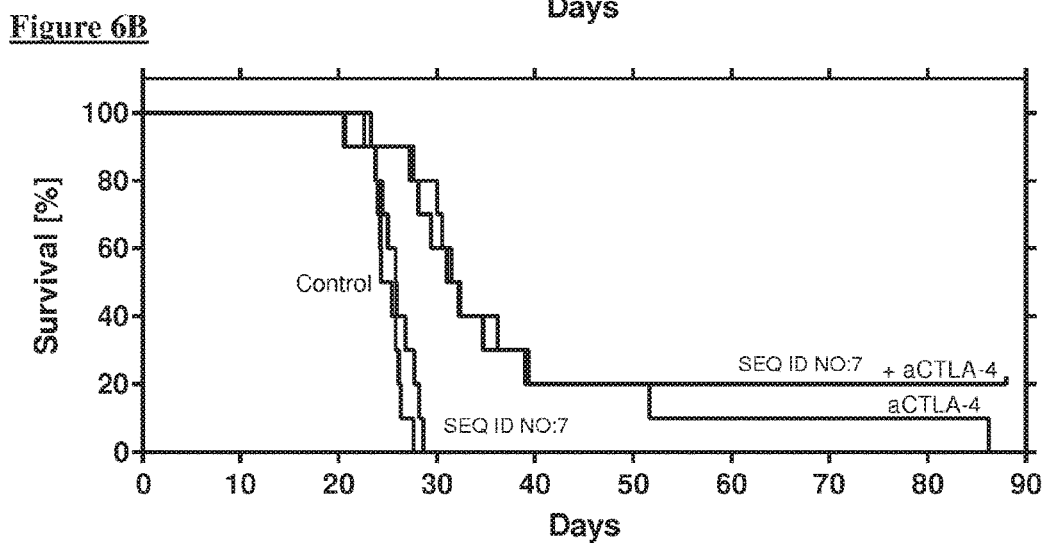

These L-nucleotide comprising molecules showed increased immune modulatory and anti-tumor properties when combined with checkpoint inhibitors. For instance, combination of SEQ ID NO:7 (GGGGTCATT AAAACGT-GACGTGACGTTCTTTTT, L-deoxyribose containing bases underlined) with anti-CTLA-4 in a mouse CT26 tumor model resulted in a surprisingly efficient decreased tumor growth compared to SEQ ID NO:7 or anti-CTLA-4 monotherapy (FIG. 6). 10 mice per group were inoculated s.c. with CT26 murine tumor cells and injected with SEQ ID NO:7 (200 µg/application, s.c. on day 3, 5, 8, 10, 12, 15, 17, 19, 22, 14 and 26), anti-CTLA-4 (100 µg/application at day 8; 50 µg/application at day 11 and 14, i.p.), or both. Injection of vehicle (s.c.) served as control. FIG. 6A shows the mean tumor growth—inlay, mean tumor growth inhibition from day 15 to 30 (at day 22: 19.8% for SEQ ID NO:7, 59.1% for anti-PD-1, 65.3% for the combination). FIG. 6B shows a Kaplan-Meier survival plot.

Figure 7A:
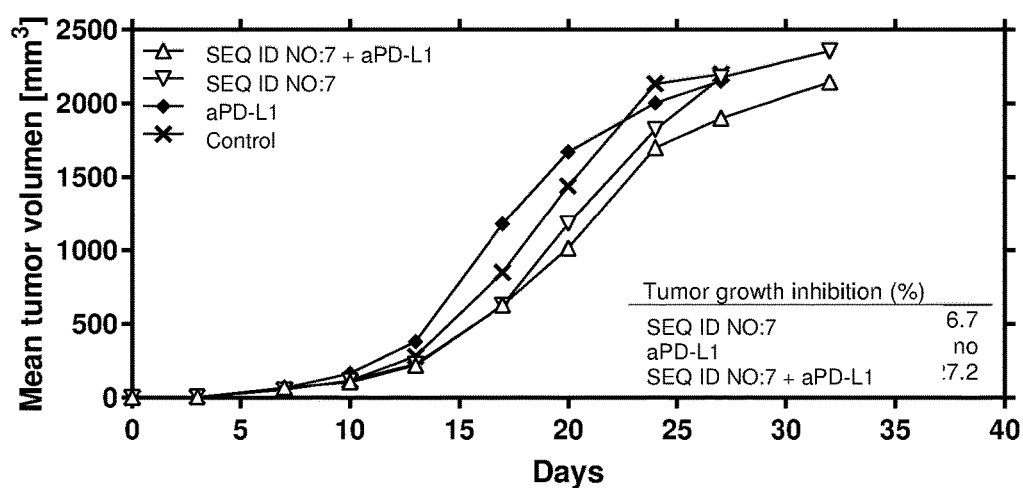
FIG. 7A, B Anti-tumor activity of the combination of SEQ ID NO:7 with anti-PD-L1.
Figure 7B:
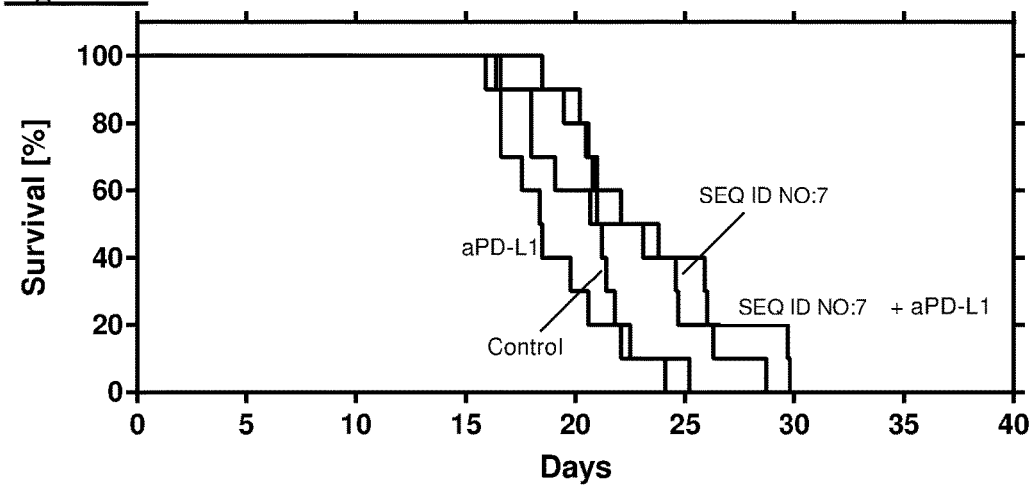

The combination of SEQ ID NO:7 with anti-PD-L1 also showed a moderately increased anti-tumor effect compared to that of the single compounds SEQ ID NO:7 or anti-PD-L1 in the mouse CT26 tumor model (FIG. 7). 10 mice per group were inoculated s.c. with CT26 murine tumor cells and injected with SEQ ID NO:7 (s.c. on day day 3, 5, 7, 10, 12, 14, 17, 19, 21, 24, and 26), anti-PD-L1 (10 mg/kg per application, i.p. on day 3, 5, 7, 9, 11, 13, 15, 17), or both. Injection of vehicle (s.c.) served as control. FIG. 7A shows the mean tumor growth—inlay, mean tumor growth inhibition from day 13 to 27 (at day 20: 16.3% for SEQ ID NO:7, no inhibition for anti-PD-L1, 33.3% for the combination). FIG. 7B shows a Kaplan-Meier survival plot.

Figure 8A:
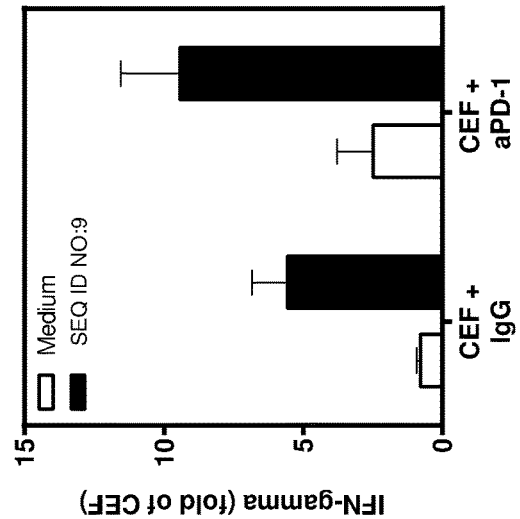
FIG. 8A-C In vitro stimulation of human PBMC with peptides selected from HLA class I-restricted T-cell epitopes of recall-antigens, SEQ ID NO:9 and anti-PD-1.
Figure 8B:
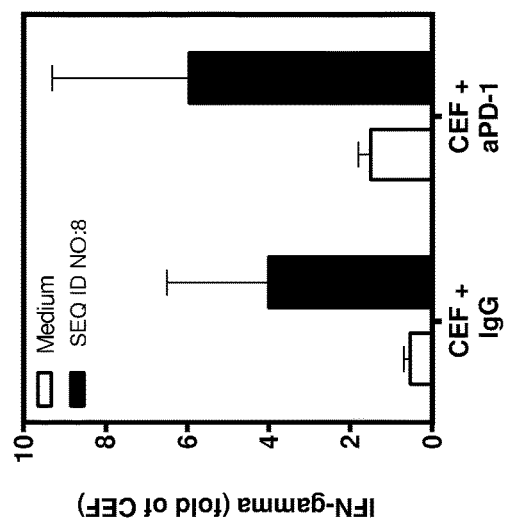
Figure 8C:
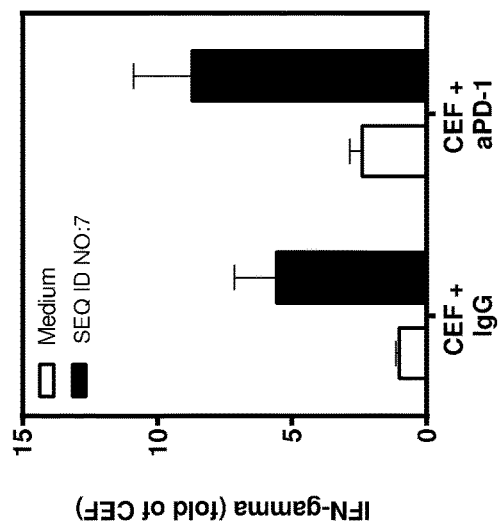

In in vitro studies the benefit of the combination of anti-PD-1 with SEQ ID NO:7, SEQ ID NO:8 (GGGGGGGGTCATTAAAACGTGACGTGACGTTCTT TTT, L-deoxyribose containing bases underlined), and SEQ ID NO:9 (GGGGTCATTAAACGTGACGTGA CGTTCTT TTT, L-deoxyribose containing bases underlined) was observed regarding IFN-gamma secretion from PBMC stimulated with antigenic peptides (FIG. 8). Peptides were selected from HLA class I-restricted T-cell epitopes of recall-antigens (CMV, EBV, Flu=CEF; final concentration 1 µg/ml per peptide), SEQ ID NO:7 (A, n=12), SEQ ID NO:8 (B, n=2), SEQ ID NO:9 (C, n=4), each DNA molecule at a final concentration of 3 µM; and anti-PD-1 (10 µg/ml). Analysis of IFN-gamma secretion as marker for immune response; normalized to IFN-gamma level after stimulation with CEF-peptides alone. Murine IgG (10 µg/ml) was used as control for anti-PD-1

In another series of experiments DNA molecules with the core sequence [yTCATTxCGTTCTTCGGGGCGTTCzv] (y=2 to 8 G, protected with 1 to 3 L-deoxyribose or not; x=3 to 4 A; z=2 to 6 T protected with 1 to 3 L-deoxyribose; v=A, G, C, T) were used.

The combinatory effect regarding immunomodulation and anti-tumor effect was established for this group as well. As example for this group, SEQ ID NO:10 (GGGGTCAT-TAAACGTTCTTCGGGG CGTTCTTTTT, L-deoxyribose containing bases bolded) was used to investigate the combination with anti-PD-1.

Figure 9A:
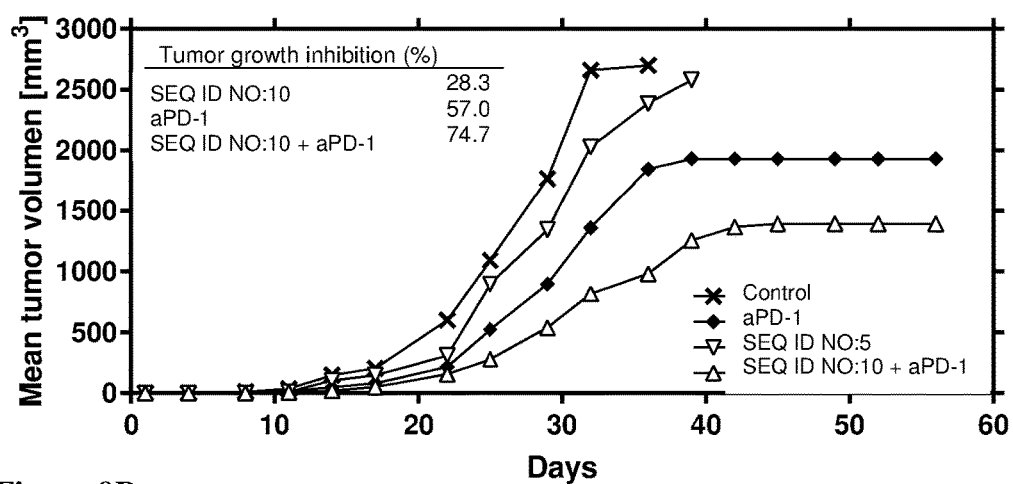
FIG. 9A, B Anti-tumor activity of the combination of SEQ ID NO:10 with anti-PD-1.
Figure 9B:
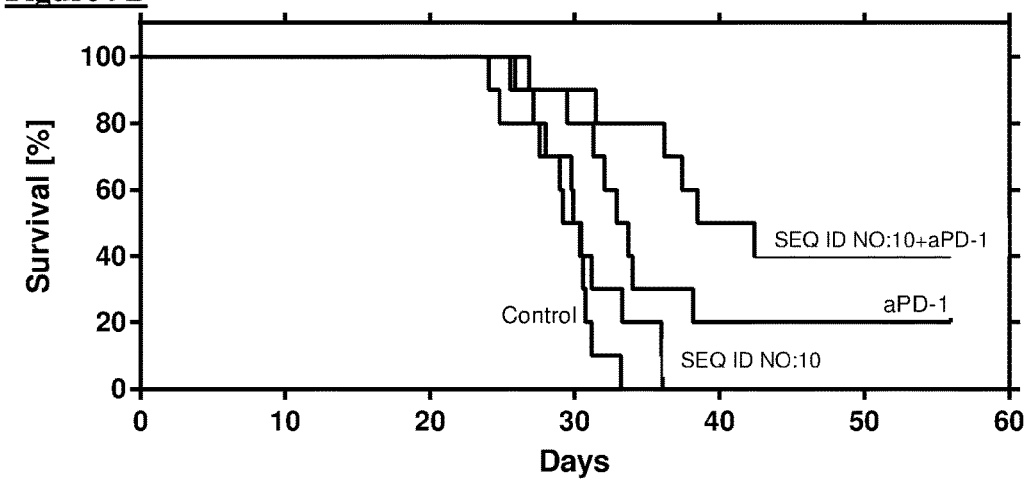

The combination resulted in a profound reduction of the tumor growth in a mouse CT26 tumor model (FIG. 9). 10 mice per group were inoculated s.c. with CT26 murine tumor cells and injected with SEQ ID NO:10 (200 µg/application, s.c. on day 3, 5, 8, 10, 12, 15, 17, 19, 22, 14 and 26), anti-PD-1 (200 µg/application, i.p. on day 3, 6, 10 and 14), or both. Injection of vehicle (s.c.) served as control. FIG. 9A shows the mean tumor growth—inlay, mean tumor growth inhibition from day 14 to 32 (at day 25: 17.8% for SEQ ID NO:10, 51.9% for anti-PD-1, 74.6% for the combination). FIG. 9B shows a Kaplan-Meier survival plot.

Figure 10A:
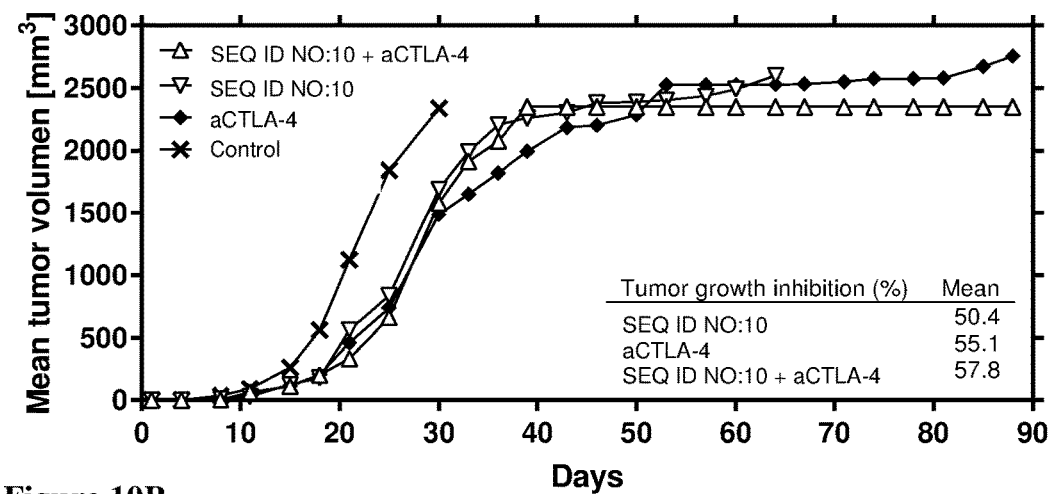
FIG. 10A, B Anti-tumor activity of the combination of SEQ ID NO:10 with anti-CTLA-4.
Figure 10B:
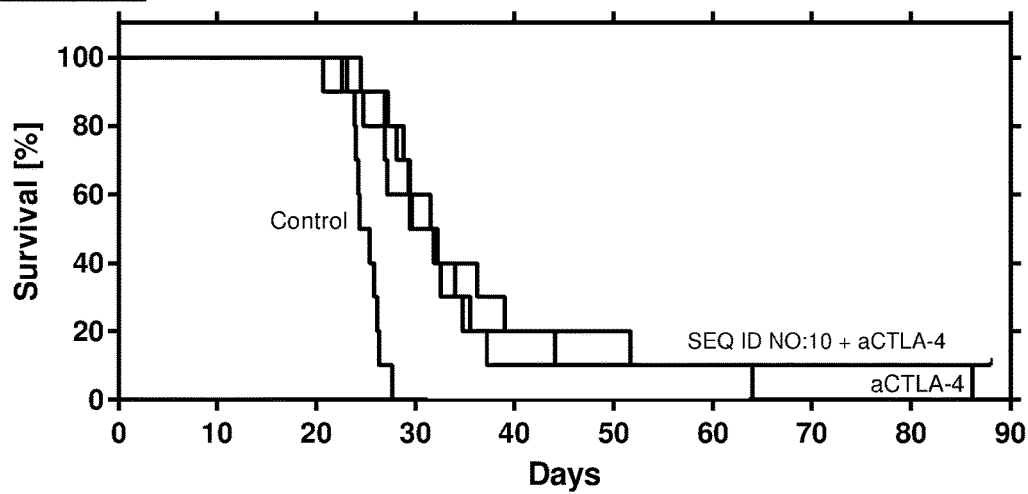

In addition, a combination of SEQ ID NO:10 with anti-CTLA-4 lead to a decreased tumor growth in mouse CT26 tumor model compared to treatment with the single agents, SEQ ID NO:10 or anti-CTLA-4 (FIG. 10). 10 mice per group were inoculated s.c. with CT26 murine tumor cells and injected with SEQ ID NO:10 (200 µg/application, s.c. on day 3, 5, 8, 10, 12, 15, 17, 19, 22, 14 and 26), anti-CTLA-4 (100 µg/application at day 8, 50 µg/application at day 11 and 14, i.p.), or both. Injection of vehicle (s.c.) served as control. FIG. 10A shows the mean tumor growth—inlay, mean tumor growth inhibition from day 15 to 30 (at day 22: 49.7% for SEQ ID NO:10, 59.1% for anti-PD-1, 70.3% for the combination). FIG. 10B shows a Kaplan-Meier survival plot.

Figure 11:
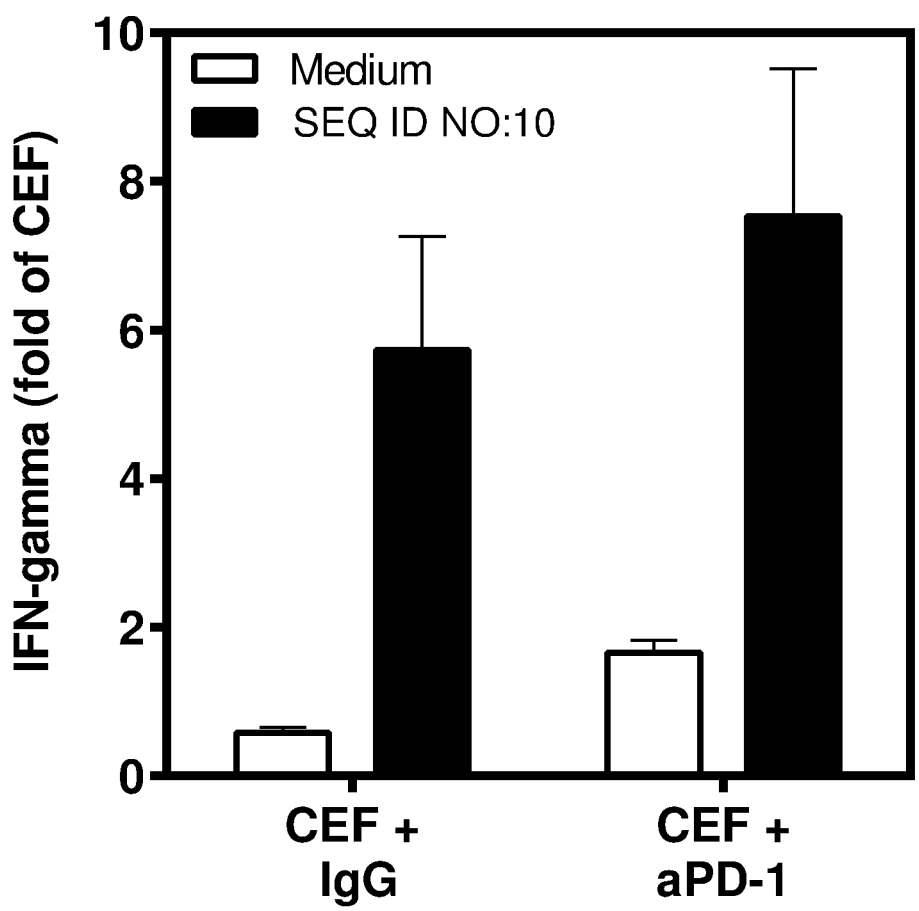
FIG. 11 In vitro stimulation of human PBMC with peptides selected from HLA class I-restricted T-cell epitopes of recall-antigens, SEQ ID NO:10 and anti-PD-1.

Furthermore, a combination of SEQ ID NO:10 and anti-PD-1 was evaluated in in vitro PBMC stimulation studies and showed an increased effect regarding IFN-gamma secretion compared to SEQ ID NO:10 or anti-PD-1 alone (FIG. 11). Peptides were selected from HLA class I-restricted T-cell epitopes of recall-antigens (CMV, EBV, Flu=CEF; final concentration 1 µg/ml per peptide)), SEQ ID NO:10 (3 µM) and anti-PD-1 (10 µg/ml) (n=5). Analysis of IFN-gamma secretion served as marker for an immune response; normalized to IFN-gamma level after stimulation with CEF-peptides alone. Murine IgG (10 µg/ml) was used as control for anti-PD-1.

In a further experiment, a DNA molecule with a core sequence [yTCATTxTCGTCGTTTTGTCGTTTTGTCGzv] (y=2 to 8 G, protected with 1 to 3 L-deoxyribose or not; x=3 to 4 A; z=2 to 6 T protected with 1 to 3 L-deoxyribose; v=A, G, C, T) was used in experiments.

Figure 12:
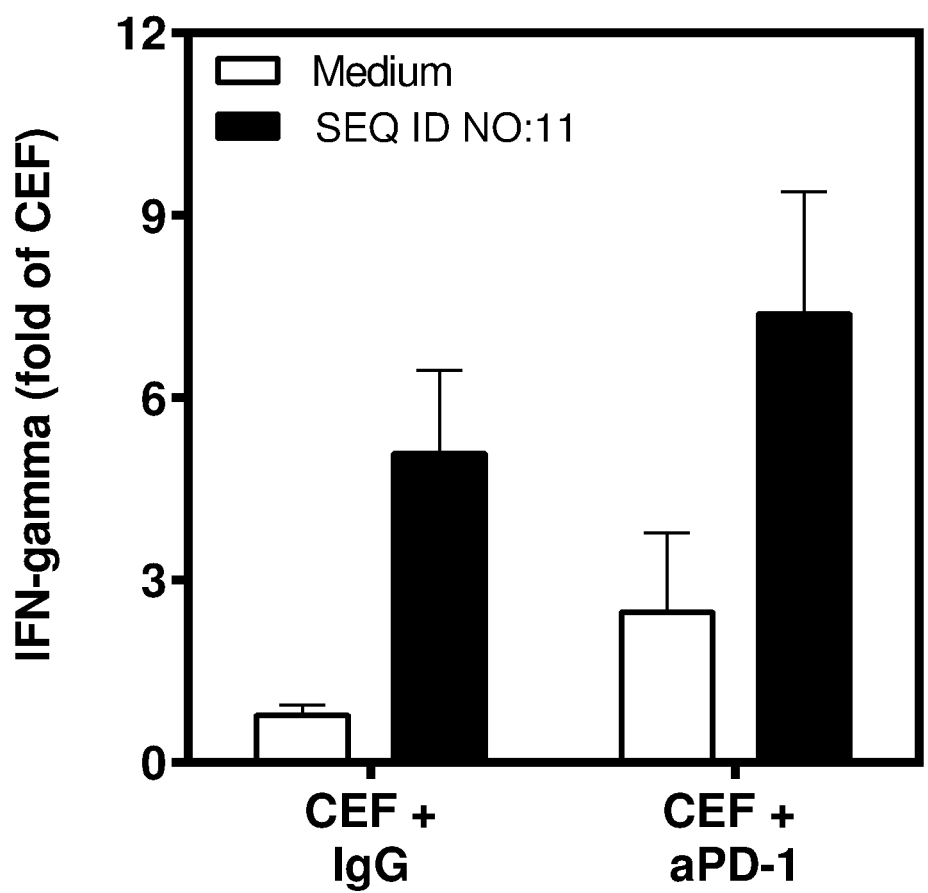
FIG. 12 In vitro stimulation of human PBMC with peptides selected from HLA class I-restricted T-cell epitopes of recall-antigens, SEQ ID NO:11 and anti-PD-1.

SEQ ID NO:11 (GGGGTCATTAAATCGTCGTTTT-GTCGTTTTGTCGTTTT, L-deoxyribose containing bases bolded) was used as example for this group. When SEQ ID NO:11 was combined with anti-PD-1 in vitro in PBMC studies, -IFN-gamma secretion surprisingly significantly increased showing an improvement compared to SEQ ID NO:11 or anti-PD-1 alone (FIG. 12). Peptides selected from HLA class I-restricted T-cell epitopes of recall-antigens (CMV, EBV, Flu=CEF; final concentration 1 µg/ml per peptide), SEQ ID NO:11 (3 µM) and anti-PD-1 (10 µg/ml) (n=4). Analysis of IFN-gamma secretion as marker for immune response; normalized to IFN-gamma level after stimulation with CEF-peptides alone. Murine IgG (10 µg/ml) was used as control for aPD-1.

Finally, a DNA molecules with the core sequence [yAC-GATCGTCwT] (y=2 to 8 G, protected with 1 to 3 L-deoxyribose or not; w=4 to 12 G protected with 1 to 3 L-deoxyribose) was used for testing effects of combinatorial application.

Figure 13:
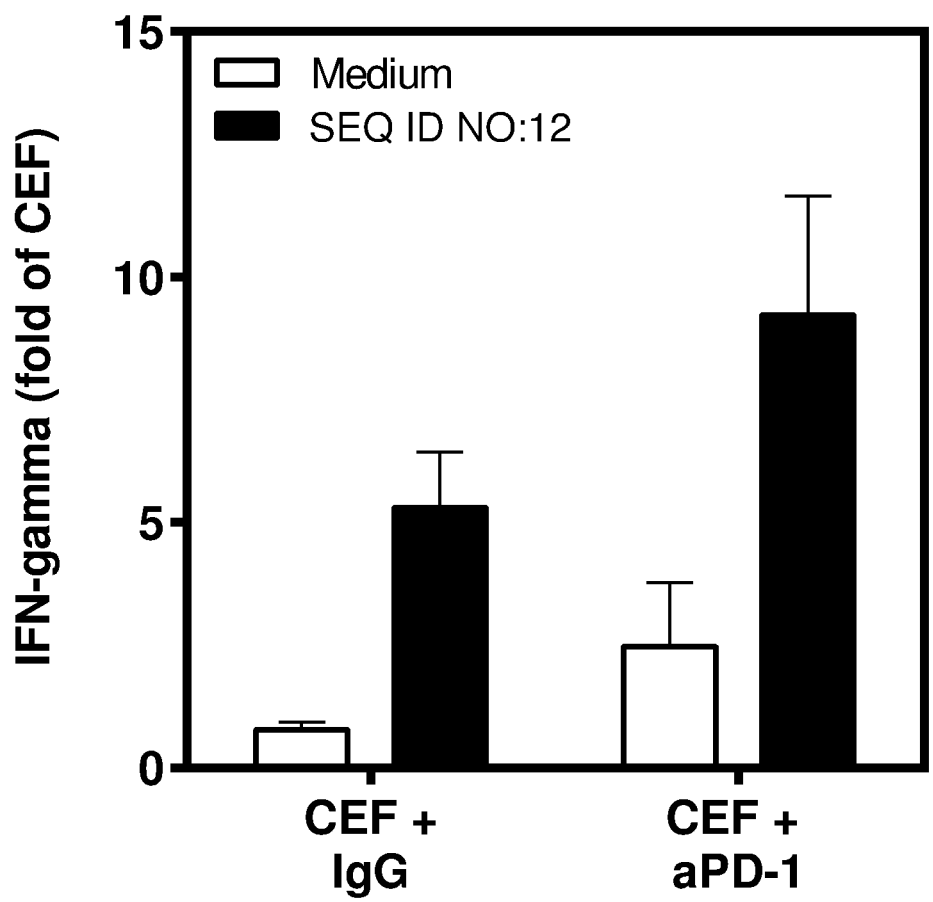
FIG. 13 In vitro stimulation of human PBMC with peptides selected from HLA class I-restricted T-cell epitopes of recall-antigens, EnanDIM362 and anti-PD-1.

An example for this group is SEQ ID NO:12 (GGGGGACGATCGTCGGGGGGT, L-deoxyribose containing bases underlined). In in vitro stimulation studies with human PBMC its combination with anti-PD-1 was evaluated leading to a significantly augmented immune response compared to the single compounds (FIG. 13). Peptides were selected from HLA class I-restricted T-cell epitopes of recall-antigens (CMV, EBV, Flu=CEF; final concentration 1 µg/ml per peptide), SEQ ID NO:12 (3 µM) and anti-PD-1 (10 µg/ml) (n=4). Analysis of IFN-gamma secretion as marker for immune response; normalized to IFN-gamma level after stimulation with CEF-peptides alone. Murine IgG (10 µg/ml) was used as control for aPD-1.

Taking the above described experimental settings into account and a weight of a mouse of about 20 g, the amounts of DNA to be applied lies in a range of about 12.5 mg/kg weight, so that it seems to be feasible that maximal 15 mg/kg will be necessary for obtaining the shown surprising results.

Anti-PD-1 antibody has been applied with 10 mg/kg weight so that the application of maximal 15 mg/kg weight also seems to be necessary for obtaining the shown surprising results.

The invention claimed is:

1. A method of treating cancer, comprising administering, to a subject in need thereof, a combination comprising the components of groups (a) and (b):
   (a) a first group comprising an antibody binding to at least one of the molecules selected from the group consisting of PD1, PD-L1 and CTLA-4 for affecting their function as T-cell regulators; and
   (b) a second group comprising a non-coding sequence of deoxyribonucleic acids comprising at least one sequence motif $N^1N^2CGN^3N^4$, wherein N is a nucleotide comprising A, C, T, or G, and C is deoxycytidine, G is deoxyguanosine, A is deoxyadenosine and T is deoxythymidine,
   wherein the non-coding sequence of deoxyribonucleic acids is either linear open-chained on both sides, linear open-chained on one side of a double stranded part with a single stranded hairpin on the respective other side of the double strand, or a dumbbell-shaped partially single-stranded covalently closed chain of deoxyribonucleic acids, and
   wherein the linear open-chained non-coding sequence of deoxyribonucleic acids comprises at least one nucleotide in L-conformation.

2. The method of claim 1, wherein the compounds of the combination are administered simultaneously, alternating or successively.

3. The method of claim 1, wherein said non-coding sequence of deoxyribonucleic acids does not comprise phosphorothioate.

* * * * *